US009067055B2

(12) United States Patent
Carrington

(10) Patent No.: US 9,067,055 B2
(45) Date of Patent: Jun. 30, 2015

(54) DEFIBRILLATOR WITH PRE-CONNECTED ELECTRODE PADS WITH REDUCED SUSCEPTIBILITY TO FALSE ASYSTOLE INDICATIONS

(75) Inventor: Christopher Carrington, Paxton, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 51 days.

(21) Appl. No.: 13/392,794

(22) PCT Filed: Aug. 18, 2010

(86) PCT No.: PCT/IB2010/053731
§ 371 (c)(1),
(2), (4) Date: Feb. 27, 2012

(87) PCT Pub. No.: WO2011/036583
PCT Pub. Date: Mar. 31, 2011

(65) Prior Publication Data
US 2012/0179234 A1 Jul. 12, 2012

Related U.S. Application Data

(60) Provisional application No. 61/246,224, filed on Sep. 28, 2009.

(51) Int. Cl.
*A61N 1/00* (2006.01)
*A61N 1/04* (2006.01)
*A61B 19/02* (2006.01)
*A61N 1/39* (2006.01)
*A61N 1/372* (2006.01)

(52) U.S. Cl.
CPC ......... *A61N 1/046* (2013.01); *A61B 2019/0267* (2013.01); *A61N 1/048* (2013.01); *A61N 1/0492* (2013.01); *A61N 1/3931* (2013.01); *A61N 1/3993* (2013.01); *A61N 2001/37294* (2013.01)

(58) Field of Classification Search
CPC . A61B 5/6833; A61B 5/04087; A61B 5/0006
USPC .............................. 607/142; 600/391; 606/32
See application file for complete search history.

(56) References Cited

U.S. PATENT DOCUMENTS 4,522,211 A * 6/1985 Bare et al. ..................... 600/392
4,850,356 A 7/1989 Heath
(Continued)

FOREIGN PATENT DOCUMENTS

WO 2008059395 A1 5/2008
WO 2008059396 A1 5/2008

*Primary Examiner* — Christopher D Koharski
*Assistant Examiner* — Philip Edwards

(57) ABSTRACT

A defibrillator electrode set for a defibrillator and a defibrillator which senses the capacitance of an attached electrode set includes an electrode set coupled to the defibrillator by an adapter cable. The adapter cable and electrode set are pre-connected to the defibrillator prior to use. The electrodes are stored in a sealed foil package to retard gel desiccation prior to use. To reduce the capacitance of the electrode set seen by the defibrillator, the capacitance between the stored electrodes and the foil package is reduced by using a thicker dielectric layer for the layer of an electrode which opposes a wall of the foil package. In a constructed embodiment, one sixteenth inch thick polyethylene foam may be used for the electrode layer opposing the wall of the foil package.

15 Claims, 9 Drawing Sheets

(56) References Cited

U.S. PATENT DOCUMENTS

| | | |
|---|---|---|
| 5,520,683 A | 5/1996 | Subramaniam et al. |
| 5,713,925 A | 2/1998 | Sullivan et al. |
| 5,984,102 A | 11/1999 | Tay |
| 6,272,385 B1 | 8/2001 | Bishay et al. |
| 2002/0072664 A1* | 6/2002 | Katzenmaier et al. ........ 600/391 |
| 2002/0082672 A1 | 6/2002 | Janae et al. |
| 2002/0117408 A1 | 8/2002 | Solosko et al. |
| 2003/0017743 A1 | 1/2003 | Picardo et al. |
| 2003/0055478 A1* | 3/2003 | Lyster et al. .................. 607/142 |
| 2006/0025823 A1 | 2/2006 | Jonsen |
| 2006/0142810 A1 | 6/2006 | Denney et al. |
| 2006/0206152 A1 | 9/2006 | Covey et al. |
| 2007/0203558 A1 | 8/2007 | Jonsen et al. |
| 2008/0210592 A1 | 9/2008 | Anderson et al. |

\* cited by examiner

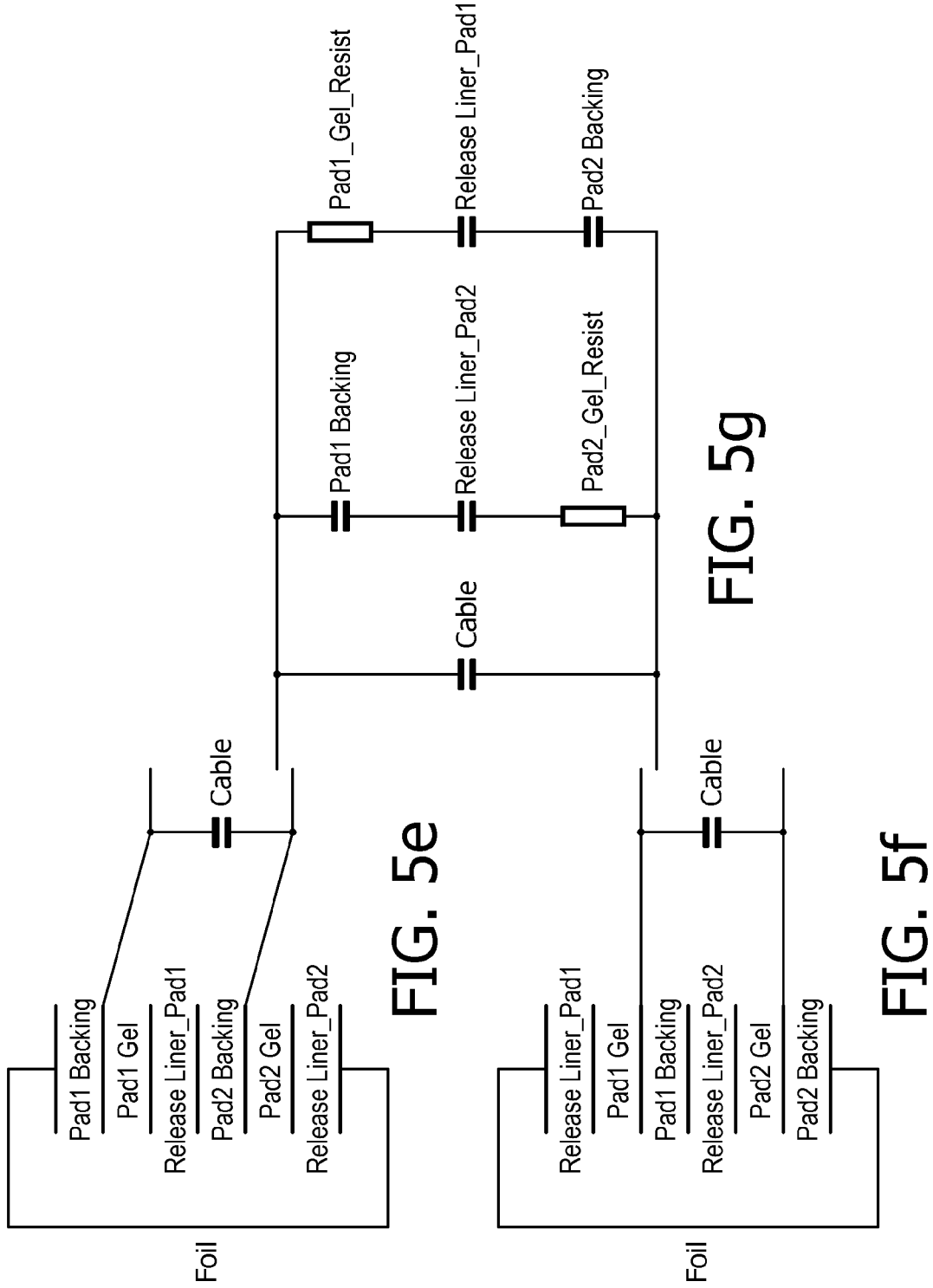

US 9,067,055 B2

DEFIBRILLATOR WITH PRE-CONNECTED ELECTRODE PADS WITH REDUCED SUSCEPTIBILITY TO FALSE ASYSTOLE INDICATIONS

This application claims the priority of international application number PCT/IB2010/053731, filed Aug. 18, 2010, which claims the benefit of U.S. provisional application Ser. No. 61/246,224, filed Sep. 28, 2009.

This invention relates to defibrillator/monitors which detect a patient's ECG signal and, in particular, to external defibrillator/monitors with pre-connected electrodes that reduce the occurrence of false asystole indications.

Defibrillators are commonly used to treat various arrhythmia by applying an electrical charge to the heart so as to disrupt the arrhythmia and allow normal electrical stimuli of the heart to spontaneously resume. Defibrillators can be implanted inside the body for chronic conditions where they can monitor the electrical activity of the heart and apply the proper electrical pulses whenever abnormal activity is detected. External defibrillators use paddles or adhesive electrodes to apply the necessary shock through the chest wall. Defibrillator/monitors not only provide defibrillation pulses, but also are able to monitor a variety of physiological parameters such as heart rate, blood pressure, and blood oxygen content, and aid in the assessment of the patient's condition after the electrotherapeutic treatment.

External defibrillators are generally not worn continuously by the patient as implantable defibrillators are, but are applied to the patient when an arrhythmia is detected. In the case of ventricular fibrillation this is usually when the patient become unconscious. Since VF is a fatal condition unless treated within minutes, emergency rescue organizations often will prepare the defibrillator for virtually immediate use when needed. One provision that can be performed is to pre-connect the electrodes to the defibrillator. Pre-connected electrodes not only avoid the electrode connection step when a medical emergency occurs, they also enable the defibrillator to self-test the condition of the electrodes during storage for defibrillators so equipped with this feature.

Automatic external defibrillators (AEDs) and advanced life support (ALS) defibrillators lend themselves to different ways of electrode pre-connection. AEDs, being small and portable, can be carried right to the patient and used alongside the patient. Since the proximity to the patient is close, the usual 3-6 foot electrode cable is all that is required. However ALS defibrillators commonly used in emergency rooms and ambulances will often be hung on a wall or carried on a cart or gurney. These defibrillators are thus often not in close proximity to the patient as an AED would be. Accordingly an adapter cable or trunk cable is frequently used to pre-connect the electrode pads to the defibrillator. The adapter cable may be 9-12 feet long which, together with the electrode pad cable, means that upwards of fifteen feet of cable may be between the defibrillator an the electrode pads.

Some defibrillators such as the Philip MRx defibrillator/monitor actively monitor the electrode connection and are able to sense when the electrodes are applied to a patient and begin ECG monitoring at once. The defibrillator/monitor can sense the impedance of the adapter cable-electrodes-patient combination connected to the defibrillator. When monitoring just the adapter cable and electrodes, the defibrillator is only seeing the capacitance of these components and the capacitance measurement should be extremely low. Under these conditions the defibrillator/monitor will produce a straight line graphic on the ECG display, since the capacitance indicates that the electrodes are not applied to a patient. When the electrodes are applied to a patient the capacitance increases above a threshold level, the patient's ECG signal is received, and the display is activated to display the ECG signal. The clinician or the defibrillator (when in automatic mode) can then begin to assess the patient's condition and begin treatment.

However it has been found that when the electrodes are pre-connected with the adapter cable, a capacitance can be produced which exceeds the threshold level, if only minimally. The defibrillator/monitor will then activate the display, replacing the straight line graphic will signals provided by the electrodes. But when the electrodes are not applied to a patient, the defibrillator will interpret the resultant low level noise as an asystole condition and can begin issuing alerts and alarms to the treating clinician. These unwarranted alerts and alarms can create disruption in what may be an already chaotic situation where a patient' life is at risk. Accordingly it is desirable to prevent the connected adapter cable and electrode combination from being viewed by the defibrillator as a patient asystole condition during pre-connection before the electrodes are applied to a patient.

In accordance with the principles of the present invention, the capacitance of an adapter cable and electrode combination pre-connected to a defibrillator is reduced, not by any change to the capacitances of the adapter cable and electrode cables, but by control of the capacitance created by the bag or pouch in which the electrodes are packaged. To provide a rugged, air-tight enclosure for the electrodes, the bag or pouch in which the electrodes are packaged is generally made of a laminated metallic foil. The present inventor has found that capacitance can be created between the electrodes and the metal of the foil bag. This capacitance will contribute to those of the adapter cable and electrode cable which are seen by the defibrillator. This capacitance is reduced by use of a high dielectric on the sides of the electrodes which oppose the walls of the foil bag or pouch, thereby preventing the sensing of excessive capacitance by the defibrillator which may be incorrectly interpreted as an asystole condition.

In the drawings:

FIGS. 5b-5g illustrate the various ways of packaging two electrode pads in a foil envelope and resulting equivalent electrical circuits.

Figure 1:
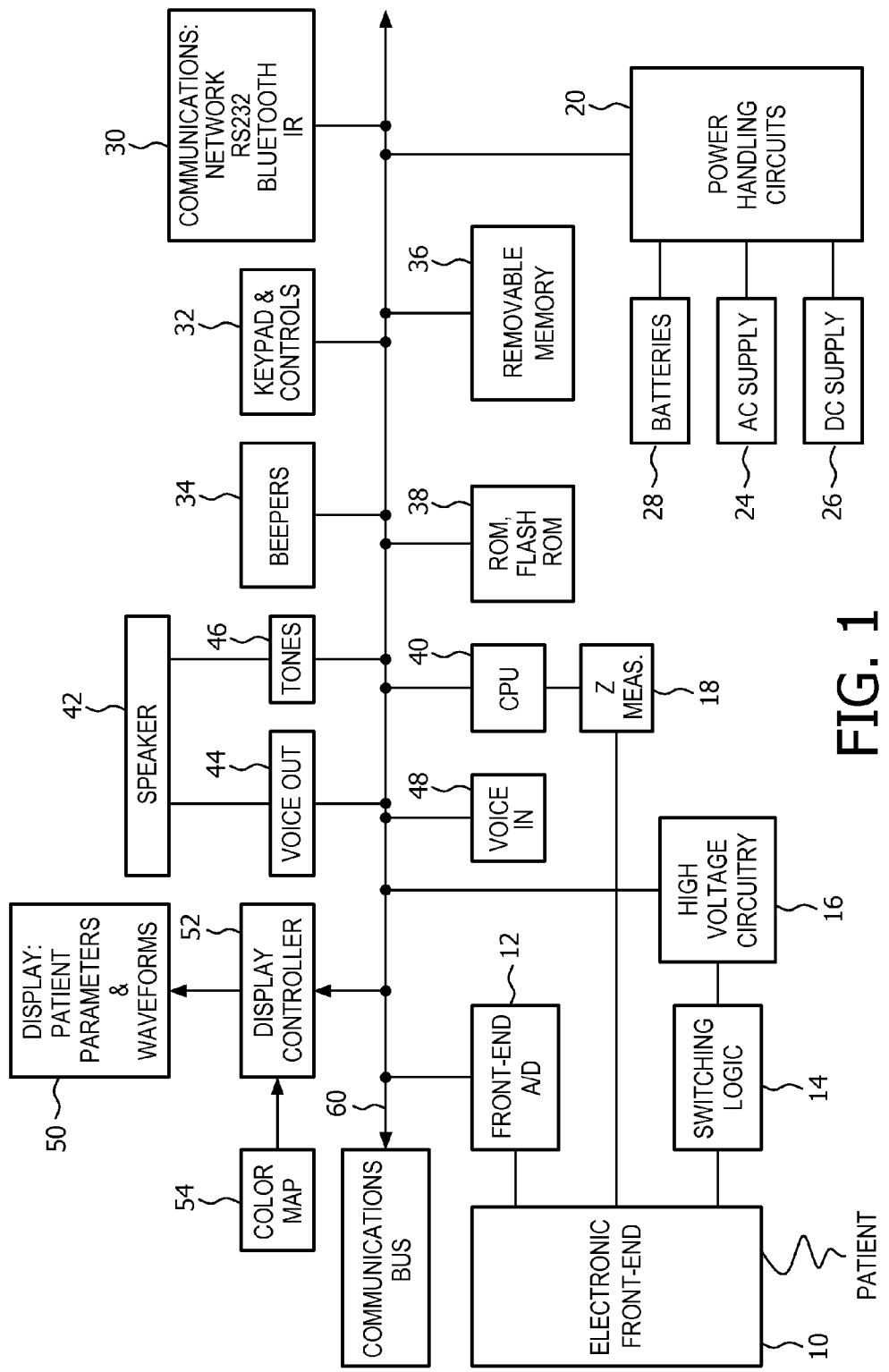
FIG. 1 illustrates in block diagram form a defibrillator/monitor constructed in accordance with the principles of the present invention.

Referring first to FIG. 1, a defibrillator/monitor constructed in accordance with the principles of the present invention is shown in block diagram form. The instrument shown in FIG. 1 is capable of performing defibrillation of a patient who is experiencing ventricular fibrillation. It is also capable of performing ECG monitoring including the cardiac monitoring necessary for automatic defibrillation decisionmaking. The illustrated monitor is also capable of $SpO_2$ oxygen sensing, noninvasive blood pressure monitoring, and end tidal $CO_2$ monitoring. Other functions such as noninvasive blood pressure monitoring and patient temperature monitoring may also be found in such a multi-functional instrument. The monitor has a plurality of patient front-ends, which are input circuitry for the sensors attached to the patient. This circuitry includes conventional sensing and amplification circuitry for ECG electrodes, for optical oxygen sensors, for pressure sensing and for carbon dioxide sensing, among others. One of the patient front-ends is input circuitry for sensing the impedance of an electrode pad set coupled to the defibrillator/monitor. The electrode connector input is coupled to an impedance measurement circuit 18 which measures the impedance of components coupled to the electrode connector input. The information received by the patient sensors and processed by the front-end circuitry 10 is digitized by front-end A/D converters 12. The digitized information is coupled to processing circuitry of the instrument by a communications bus 60 which connects data between the various modules of the instrument.

The instrument includes high voltage circuitry 16 for defibrillator operation. The high voltage circuitry produces the high voltage pulse necessary for defibrillation which is connected at the appropriate time by switching logic 14 to defibrillator electrodes coupled to the patient. In an implementation of the present invention, these defibrillator electrodes are those used to receive the patient's ECG signal prior to delivery of a defibrillation pulse. The high voltage circuitry provides the high voltage shock needed to disrupt the ventricular fibrillation and return the heart to a normal rhythm. The shock level and waveform delivered for defibrillation can be automatically calculated by a processor in the monitor or can be manually set by an experienced medical technician or physician.

Power for the modules within the instrument is distributed by power handling circuits 20. The power handling circuits 20 will distribute power from batteries 28, from an AC supply 24, or from a DC supply 26. The AC and DC supplies are also coupled to circuitry which charges the batteries when the monitor is powered from these external power sources.

The information obtained by the instrument may be sent to other instruments or locations by communications circuitry 30. This may include a network connection, an RS232 connection, or a wireless connection (e.g. Bluetooth, WiFi or infrared, etc.).

The instrument is operated and adjusted by means of a keypad and controls 32. In a constructed embodiment the keypad is a membrane keypad providing integrity against environmental conditions. Controls such as an on/off switch, power level and shock delivery controls for defibrillation, a printer, and other functions may also be provided.

The monitor is operated under control of a central processing unit (CPU) 40. The CPU runs software stored on a read-only memory (ROM) 38. Flash ROM is also provided for the control of feature setups and new or special capabilities such as waveform information. Removable memory 36 is provided for storage of information generated during a patient episode such as ventricular fibrillation. Patient information such as cardiac waveforms before and after defibrillation are also stored on the removable memory 36, which can be removed and given to a subsequent care-giver for review, record-keeping, and subsequent diagnosis. The removable memory 36 could also record voice information from a care-giver speaking into a microphone 48.

Beepers 34 are used to drive a solid-state sound source that produces short "chirping" sounds. These sounds indicate that the instrument's resident self-test has detected a low battery level or a malfunction in a patient-critical circuit group. There is also a dedicated display on the front of the instrument that presents a large, flashing, red X to indicate a low battery level or a large, fixed, red X to identify a circuit failure.

Tones 46 are produced by the software and then used to drive the speaker 42. This capability is used during certain monitoring functions such as a short tone in response to each heart cycle. Combinations of tones are used to issue audible alerts and alarms when a patient's vital measurements fall outside the alarm limits selected.

The speaker 42 can reproduce pre-recorded voice instructions and information stored and reproduced from voice out circuitry 44.

A display 50 is provided for the display of patient parameters and waveforms as discussed more particularly below. The information to be displayed is provided to a display controller 52 which provides the necessary drive signals for display of the information on the display. In a constructed embodiment the display is a color LCD display, although other types of display such as a CRT display may be used in a particular embodiment. The display controller 52 displays information in accordance with a color map provided by color map store 54. In a constructed embodiment the color map is stored in tabular form. In other embodiments the color map may be stored as an algorithm or other programmed information.

Figure 2:
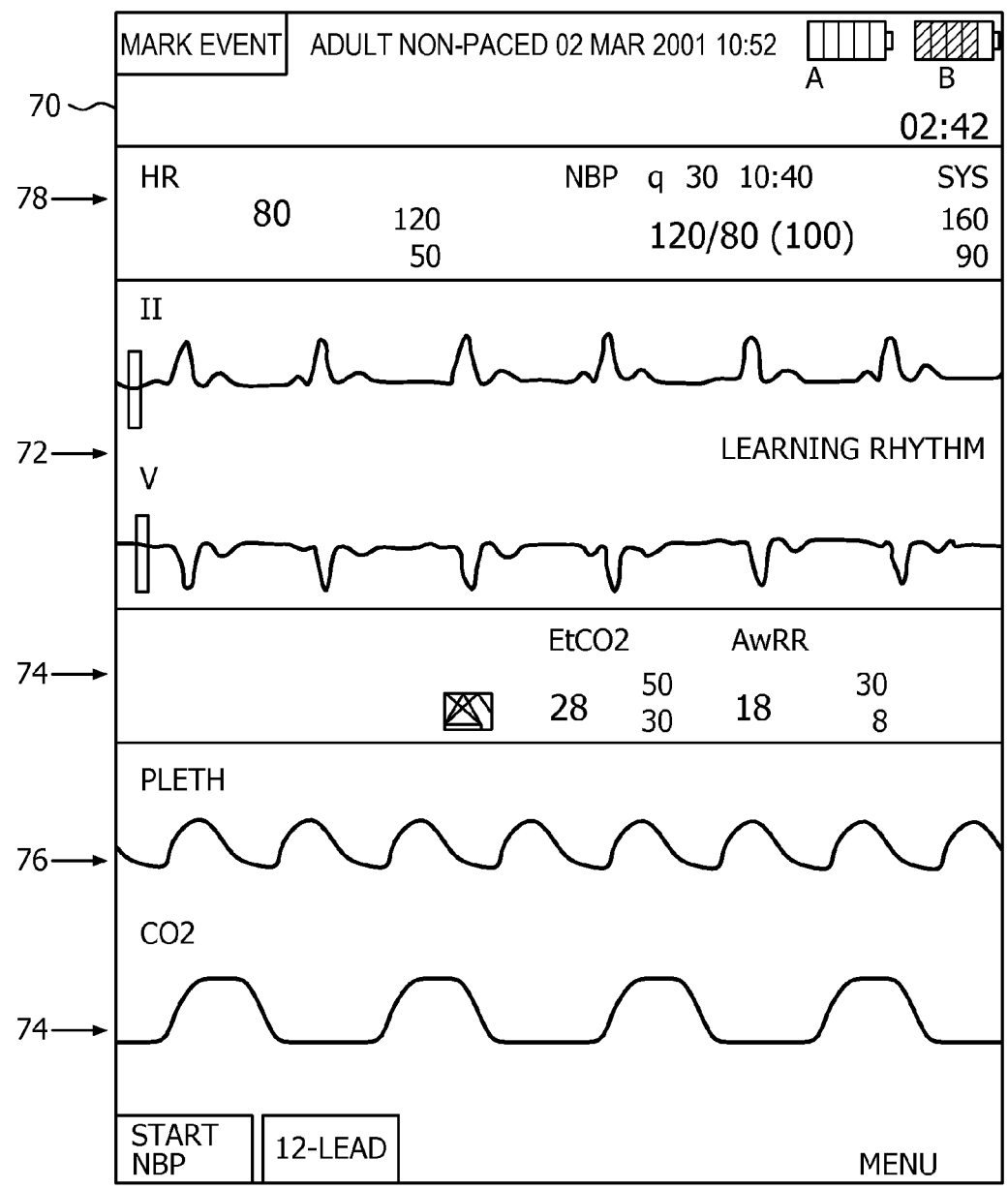
FIG. 2 illustrates the display of the defibrillator/monitor of FIG. 1.

FIG. 2 illustrates the display 70 of a monitor constructed in accordance with the principles of the present invention during normal operation as might be found inside a hospital. Under such room light conditions the background of the display 70 is black, or gray as indicated by reference numeral 78. The graphical information at the very top of the display 70 is displayed in white against the black background. To readily distinguish and associate the different types of information displayed, the numerical and graphical information is displayed in color. For instance the numerical heart rate 80 and the heart traces below as indicated at 72 are displayed in green. The numerical $CO_2$ reading of 28 and the $CO_2$ trace indicated at 74 are displayed in light blue. The plethysmograph trace 76 is displayed in purple. Such a color display against a black or gray background has been found to be pleasing to view in an indoors environment where ambient light conditions are not high.

Figure 3:
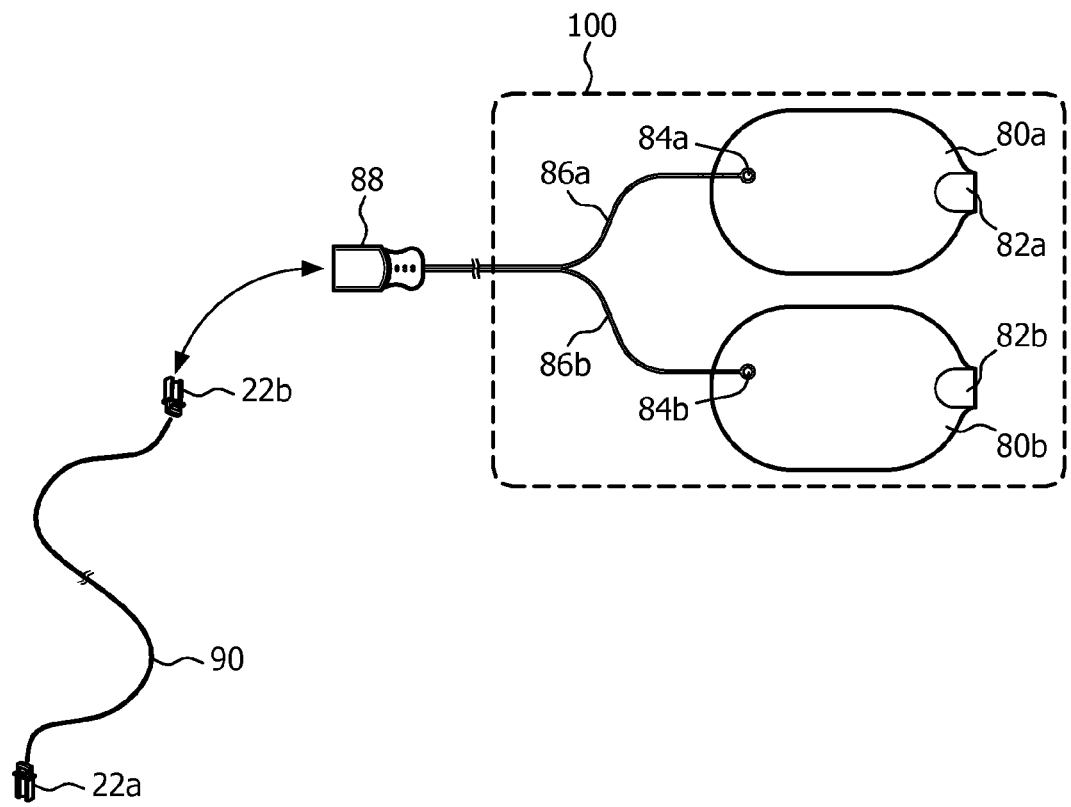
FIG. 3 illustrates an adapter cable and electrode set constructed in accordance with the principles of the present invention.

FIG. 3 illustrates a packaged electrode set and adapter cable which may be connected to the electrode input of the defibrillator/monitor of FIG. 1. The adapter cable 90 which is typically 3-5 meters in length has a connector 22a at one end which plugs into the electrode connection socket of the defibrillator and a connector 22b at the other end which connects to the connector 88 of the electrode set as indicated by the arrow. The adapter cable has two conductors, one for each electrode of the electrode set.

The electrode set includes two electrodes 80a and 80b. Each electrode has a wire 86a, 86b connected to it by a fastener 84a, 84b. The wires 86a, 86b terminate at the electrode set connector 88 which electrically couples them to the wires of the adapter cable 90. Each electrode is covered by a release liner which protects the patient-contacting conductive adhesive gel surface from contamination prior to use. At the end of each release liner is a tab 82a, 82b which may be grasped by a rescuer to peel the release liner away from the adhesive gel. The electrodes are sealed in a laminated foil envelope 100 prior to use, which is sealed around the wires 86a, 86b where they exit the envelope.

Figure 4:
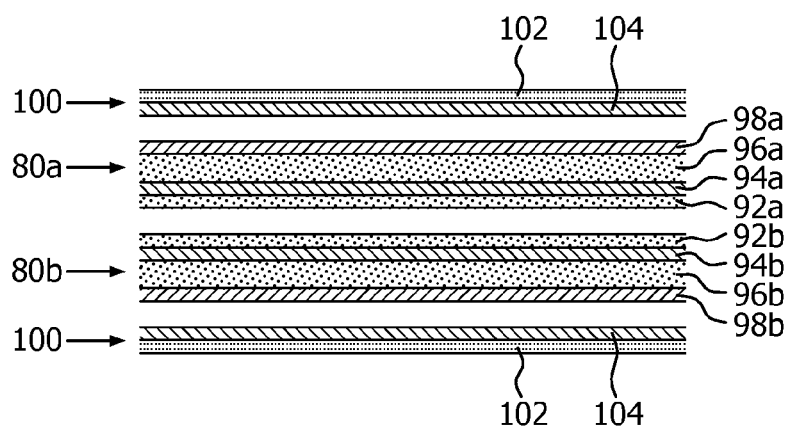
FIG. 4 is a partial cross-sectional view of the packaged electrodes of FIG. 3.

FIG. 4 is a partial cross-sectional view of the electrodes 80a, 80b and the foil envelope 100 in which they are stored prior to use. The walls of the envelope are on either side of the packaged electrodes, including an outer polymeric layer 102 which is laminated to the inner foil layer 104. Inside the foil envelope are the two electrodes 80a, 80b. In this example the electrodes are stored in the envelope with their backing layers in contact with each other and their release liners opposing the respective walls of the envelope. Each electrode has a nonconductive backing layer 92a, 92b which is adhered to a metallized electrode layer 94a, 94b, which may be formed, for instance, of tin. Covering the electrode layer is a layer of conductive adhesive gel 96a, 96b. Covering the gel layer to protect it before use is a release liner 98a, 98b. Typically such release liners are formed of treated Kraft paper or a polymer sheet which enables the release liner to be easily peeled off of the adhesive gel. Since the release liner layers only serve to cover the surface of the gel layer and is disposed of when removed, it is generally made of one of these thin, inexpensive materials. However, in accordance with the principles of the present invention, the release liner layers 98a, 98b in the example of FIG. 4 are made of a polyethylene foam which is significantly thicker than the typical release liner sheet. Instead of a typical thickness of seven thousandths of an inch, the foam release liner layers 98a, 98b are a sixteenth of an inch (0.0625") thick.

Figure 5A:
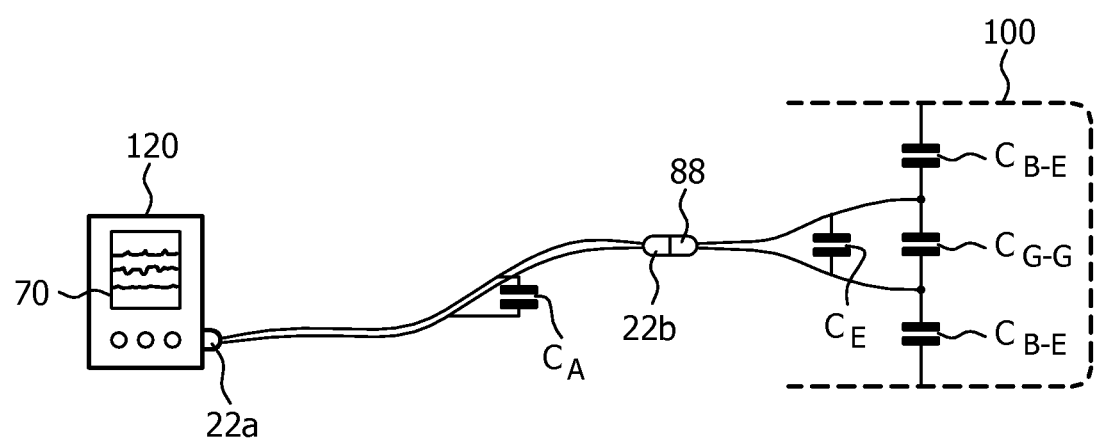
FIG. 5a illustrates the capacitances which may be seen by a defibrillator monitor when pre-connected to an adapter cable and electrode set.

The effect of this increased thickness of the electrode layer opposing the foil envelope can be appreciated from FIG. 5a. The typically thin release liner layer will act as the dielectric layer of a capacitance, where the plates of the capacitance are the conductive gel on one side and the foil of the envelope on the other. The typically thin release liner will provide a thin dielectric and hence a sizeable capacitance. But in this example of the present invention, the release liner is made thicker by the greater thickness of the polyethylene foam. The thicker dielectric layer of the release liner will reduce the capacitance and hence the contribution of this capacitance to the overall capacitance of the adapter cable 90 and the electrode set 80a, 80b. FIG. 5a illustrates these capacitances in the instance where the electrodes are stored in the foil envelope with their release liners in contact with each other and their backing layers opposing the walls of the foil envelope. In this case there is a capacitance $C_{B-E}$ between each electrode backing and the opposing wall of the foil envelope, where the metallic sheet 94a, 94b is one plate of the capacitance and the metallic sheet of the envelope 100 is the other plate. To reduce this capacitance the dielectric between these plates, the backing 92a, 92b of each electrode, is made thick such as by using one-sixteenth inch thick polyethylene foam for the backing material. The capacitance in the center of the package, $C_{G-G}$ between the gel layers 96a, 96b, can be reduced by using a thicker dielectric of this capacitance, the release liners 98a, 98b of each electrode. The capacitance $C_E$ is the capacitance of the electrode set absent the foil package 100, and the capacitance $C_A$ is the capacitance of the adapter cable 90. By using thick materials for the release liners and/or the backing layers of the electrodes, the capacitances $C_{B-E}$ and $C_{G-G}$ can be reduced, thereby reducing the overall capacitance seen by a defibrillator 120 to which the adapter cable connector 22a is connected.

Figures 5B, 5C, 5D:
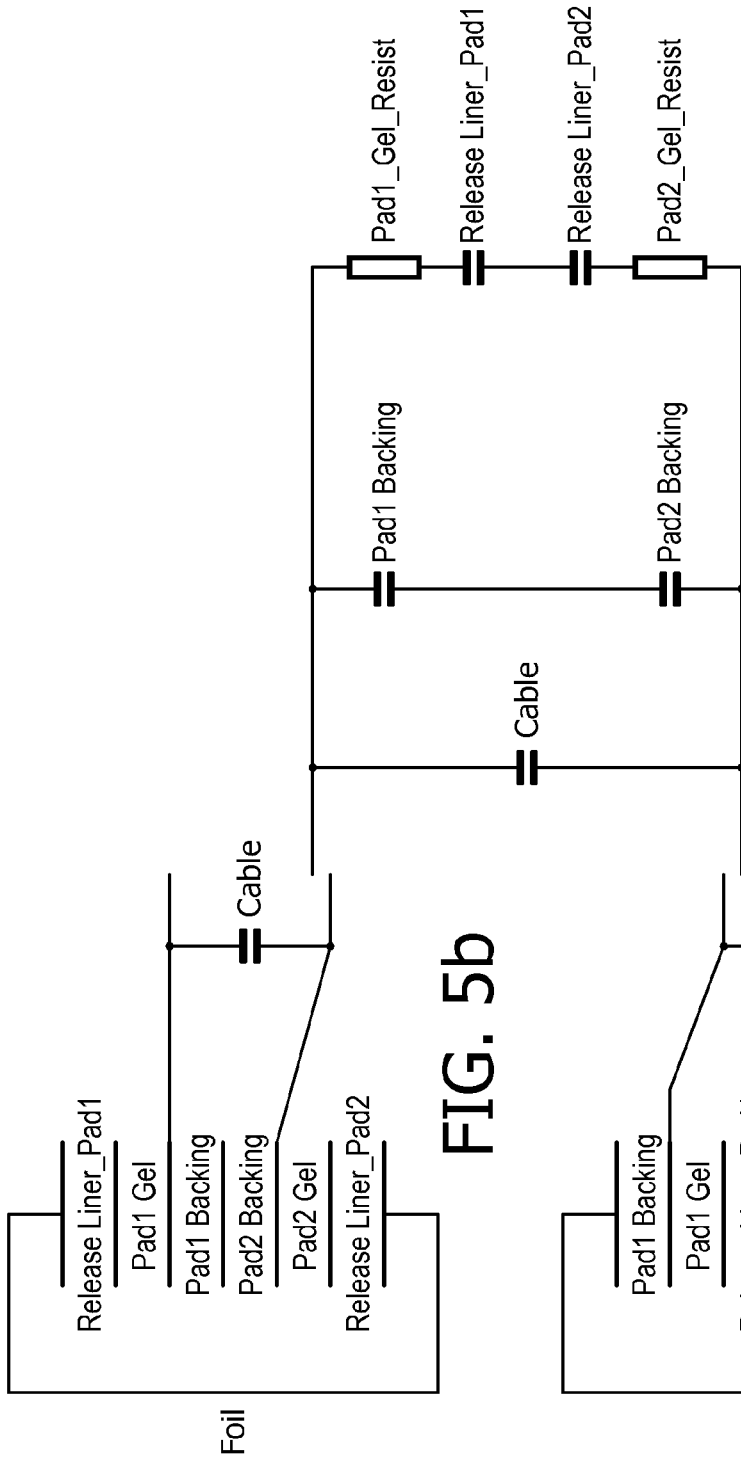

FIGS. 5b and 5c illustrate two ways in which a pair of electrode pads can be positioned in a foil envelope. In FIG. 5b the backing layers of the two pads are in contact with each other, which means that the release liners oppose the walls of the envelope. FIG. 5c illustrates a second positioning of the electrode pads, in which the release liners of the two pads are in contact with each other and the backing layers of the pads oppose the walls of the foil envelope. FIG. 5d is an equivalent electrical circuit showing the effective resistances and capacitances when the pads are packaged as shown in FIG. 5b.

FIGS. 5e and 5f illustrate two other ways in which a pair of electrode pads can be positioned in a foil envelope. In FIG. 5e the release liner of the upper pad is in contact with the backing layer of the lower pad. In FIG. 5f the backing layer of the upper pad is in contact with the release liner of the lower pad. FIG. 5g is an equivalent electrical circuit showing the effective resistances and capacitances when the pads are packaged as shown in FIG. 5f.

Figure 6:
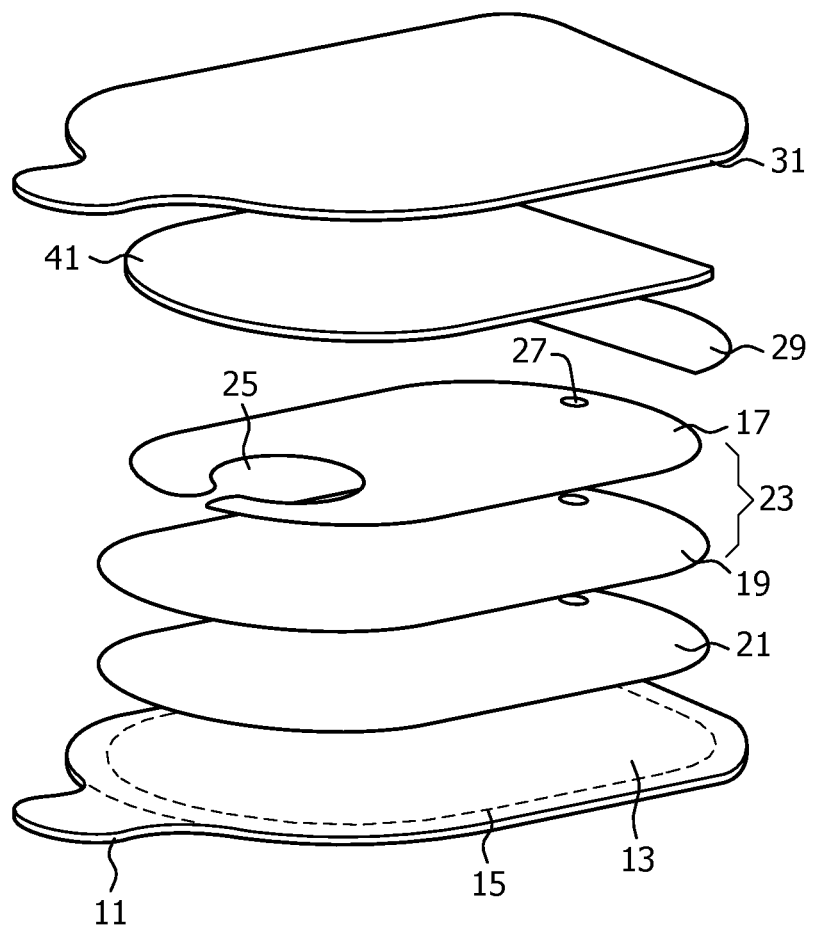
FIG. 6 illustrates the construction of an electrode pad of the present invention.

FIG. 6 is an exploded view of another defibrillator electrode constructed in accordance with the principles of the present invention. A foam backing layer 13 has a pull tab 11 at one end for separating the release liner from the electrode. In this example the periphery of the backing layer 13 is sealed to the release liner to form a moisture-proof compartment for the gel layer between the backing layer and the release liner, both of which are impervious to moisture in this example. The other layers of the electrode are overlaid inside the dashed line 15 of the backing layer 13. A conductive layer 23 is formed of a tin layer 17 and a reinforcement layer 19 of polymeric material over which the tin layer is laminated. The conductive layer 23 is attached to the backing layer 13 by a layer 21 of adhesive. These layers have a hole 27 through them for insertion of a rivet (not shown) to which the electrode wire is swaged. A rivet cover 29 overlays the rivet to prevent direct contact of the rivet to the skin of the patient. An electrically conductive gel layer 41 overlays the rest of the conductive layer 23. The electrode is covered by a release liner 31 which is then peripherally sealed to the periphery of the backing layer 13. To provide thick dielectric layers for capacitances between the electrodes or between the electrodes and a foil package, the release liner 31 and/or the backing layer 13 are formed of a thick material such as a polymeric foam layer. It will be appreciated that if the electrodes are to be consistently packaged in their foil pouch with the backing layers always opposing the walls of the package, then it would only be necessary to use thick dielectric material for the backing layers, assuming that the gel-to-gel capacitance across the release liners was minimal. If the electrodes were going to be packaged with the release liners always opposing the foil walls of the package, then it is the thickness of the release liners that would take on greater importance. Of course, if both the release liners and the backing layers of the electrodes are made of thick dielectric material, then there would need be no concern over the electrode orientation as they were packaged.

Figure 7:
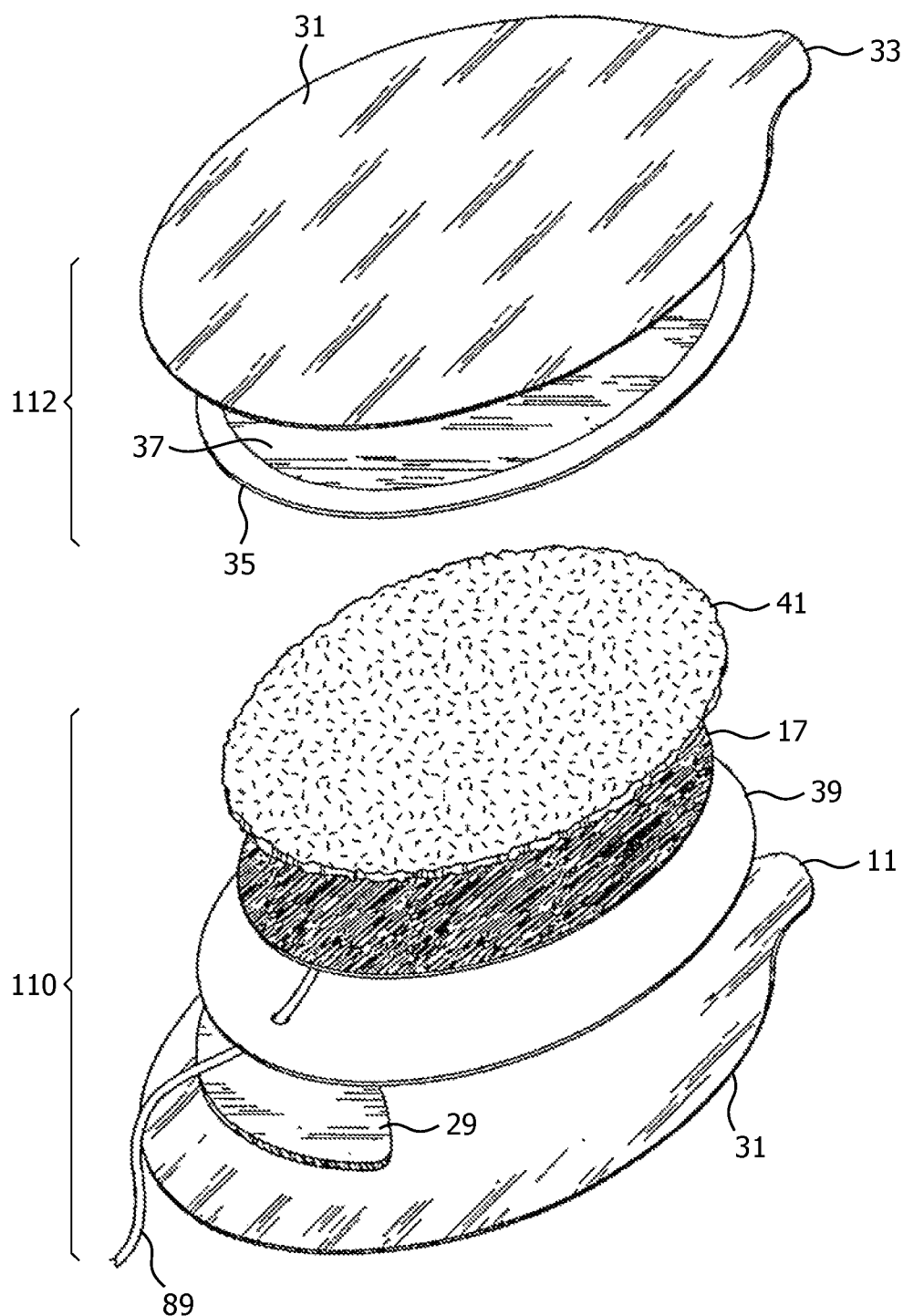
FIGS. 7 and 8 illustrate the construction of another electrode pad set in accordance with the principles of the present invention.
Figure 8:
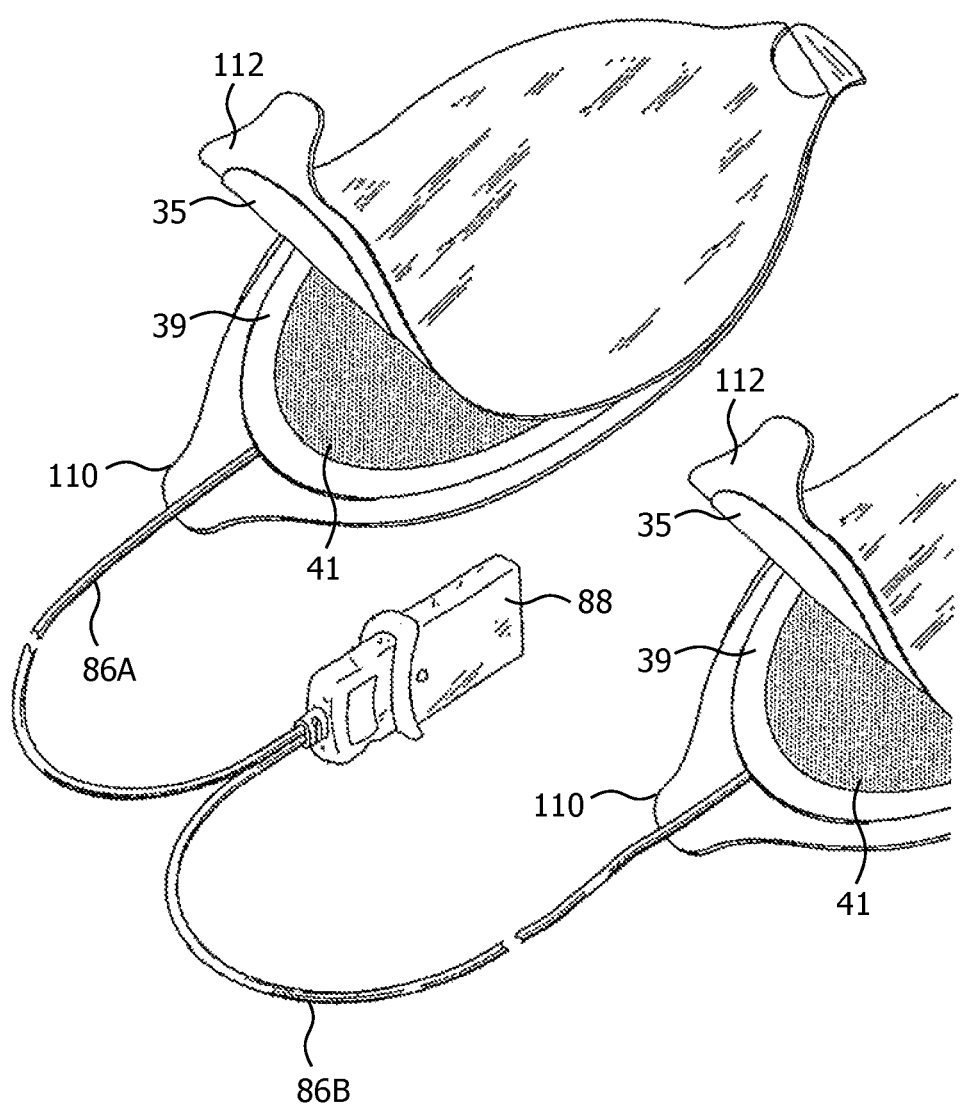

FIGS. 7 and 8 illustrate another example of an electrode set of the present invention in which the backing and/or the release liner layers are of a two-ply construction, enabling the thickness of a ply to be chosen for the desired dielectric properties of the layer. In this example a gel layer 41 overlays an electrode disk 17 to which an electrode wire 86 is attached. A rivet cover 29 overlays the portion of the layers where the electrode wire 86 is attached. The layers are attached to a backing layer 13 which has a pull tab 11 at one end. Between the electrode disk 17 and the backing layer 13 is a nonconductive barrier layer 39 which is attached to both the electrode disk and the backing layer. The thickness of this barrier layer 39 can be chosen to provide a desired reduced capacitance between the electrode disk and any metallic material outside the backing layer such as the wall of a foil storage pouch.

The release liner is similarly of a layered construction. A nonconductive release liner layer 31 with a pull tab 33 is attached by an adhesive layer to a second barrier layer 35. The thickness of this barrier layer 35 may be chosen to provide the two-ply release liner with a thickness that will provide a desired dielectric thickness between the gel layer 41 and any metallic layer opposing the release liner during storage of the electrode. FIG. 8 illustrates two such electrodes with their wires 86A, 86B coupled to an electrode connector 88 and with the two-ply release liners 112 partially peeled away from their electrodes and gel layers 41. In the example of FIGS. 7 and 8, the same materials can be consistently used for the backing layers and release liners, with barrier layers of selected thicknesses used to provide the desired dielectric properties for the electrodes. Either the backing layer or the release liner or both may be formed of a two-ply construction as desired in a given implementation.

What is claimed is:

1. A defibrillation electrode set comprising:
   an adapter cable having a first capacitance;
   a pair of electrodes, each comprising a plurality of layers having a second capacitance and including
     a metallic layer,
     a backing layer adhered to the metallic layer,
     a gel layer overlaying the metallic layer, and
     a release liner layer having a thickness of about one-sixteenth of an inch or more covering the gel layer; and
   a foil envelope configured to enclose and store the electrodes prior to use,
   wherein at least one of the plurality of layers is configured to have a thickness providing a third capacitance for which the at least one of the plurality of layers is a dielectric,
   and wherein a combination of the first, second, and third capacitances does not exceed an asystole condition.

2. The defibrillation electrode set of claim 1, wherein the layer with the configured thickness is the release liner layer.

3. The defibrillation electrode set of claim 1, wherein the layer with the configured thickness is the backing layer.

4. The defibrillation electrode set of claim 3, wherein the backing layer and the release liner both comprise a configured thickness.

5. The defibrillation electrode set of claim 1, wherein the thickness of the backing layer is ten-thousandths of an inch.

6. The defibrillation electrode set of claim 1, wherein the thickness of the backing layer is one-sixteenth of an inch or more.

7. The defibrillation electrode set of claim 1, wherein the release liner layer comprises polyethylene foam.

8. The defibrillation electrode set of claim 1, wherein the backing layer comprises the configured thickness of one-sixteenth of an inch.

9. The defibrillation electrode set of claim 8, wherein the release liner layer includes a thickness of ten-thousandths of an inch.

10. The defibrillation electrode set of claim 8, wherein the release liner layer includes a thickness of about one-sixteenth of an inch.

11. The defibrillation electrode set of claim 8, wherein the backing layer comprises a polyethylene foam.

12. The defibrillation electrode set of claim 1, further comprising a connector having a capacitance measurement circuit and configured to connect to the adapter cable,
    wherein the capacitance is compared to a threshold level.

13. The defibrillation electrode set of claim 12, wherein signals are produced when the capacitance exceeds the threshold.

14. The defibrillation electrode set of claim 12, wherein a graphic line of an ECG display is displayed when the capacitance is below the threshold.

15. The defibrillation electrode set of claim 12, wherein each electrode further comprises a fastener and a wire for electrically coupling the metallic layer to the connector.

* * * * *